(12) United States Patent
Liu et al.

(10) Patent No.: US 6,608,193 B2
(45) Date of Patent: Aug. 19, 2003

(54) METHODS FOR SYNTHESIS OF AMINO-TETRAHYDROISOQUINOLINE RING COMPOUNDS

(75) Inventors: Song Liu, San Diego, CA (US); William Martin Rennells, Schenectady, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/028,227

(22) Filed: Dec. 21, 2001

(65) Prior Publication Data

US 2002/0077480 A1 Jun. 20, 2002

(51) Int. Cl.⁷ .............................................. C07D 217/12
(52) U.S. Cl. ....................... 540/555; 540/559; 546/62; 546/81; 546/84
(58) Field of Search ................ 514/219, 220; 540/555, 559; 546/62, 81, 84

(56) References Cited

U.S. PATENT DOCUMENTS

| | | | |
|---|---|---|---|
| 5,817,751 A | 10/1998 | Szardenings et al. | 530/317 |
| 5,962,471 A | 10/1999 | Schudok et al. | 514/309 |

FOREIGN PATENT DOCUMENTS

| | | | | |
|---|---|---|---|---|
| WO | WO 97/17344 A1 | * | 5/1997 | C07D/409/12 |
| WO | WO 98/16526 A1 | * | 4/1998 | C07D/471/04 |

OTHER PUBLICATIONS

Van Loevezijn A., et al.; "Solid Phase Synthesis of Fumitremorgin, Verruculogen and Tryprostatin Analogs based on a Cyclization/Cleavage Strategy"; *Tetrahedron Letters*, 1998, pp. 4737–4740, vol. 39.

Fantauzzi P. P. et al.; "Synthesis of Diverse Tetrahydro–β–Carboline–3–Carboxamides and —2,3–Bis–lactams On a Versatile 4 Hydroxythiophenol—Linked Solid Support", *Tetrahedron Letters*, 1998, pp. 1291–1294, vol. 39.

* cited by examiner

Primary Examiner—Zinna Northington Davis
(74) Attorney, Agent, or Firm—Holly D. Kozlowski; David V. Upite

(57) ABSTRACT

Methods of preparing amino-substituted-tetrahydroisoquinoline ring compounds include the steps of providing a support-bound amino-substituted-tetrahydroisoquinoline compound; forming an intermediate by reacting the support-bound amino-substituted-tetrahydroisoquinoline compound with a reagent; and cyclizatively cleaving the support-bound amino-substituted-tetrahydroisoquinoline compound to form the amino-substituted-tetrahydroisoquinoline ring compound.

22 Claims, No Drawings

METHODS FOR SYNTHESIS OF AMINO-TETRAHYDROISOQUINOLINE RING COMPOUNDS

FIELD OF INVENTION

The present invention relates to methods of preparing amino-tetrahydroisoquinoline ring compounds. More particularly, the invention relates to the synthesis of amino-substituted-carboxylic acid ring compounds using a solid support. The invention also relates to methods of preparing combinatorial libraries of amino-substituted-carboxylic acid ring compounds.

BACKGROUND ART

The amino-substituted-tetrahydroisoquinoline-carboxylic acids (amino-substituted-TIQ-carboxylic acid) are useful in numerous pharmaceutical applications. Such compounds have been useful in treatment of degenerative joint disorders, disorders of the connective tissue, ulcerations, atherosclerosis, stenosis, inflammation, carcinomatosis, anorexia, and septic shock. Thus, it is desirable to generate derivatives of amino-substituted-TIQ-carboxylic acid such as ring-containing tetrahydroisoquinoline compounds, referred to as amino-substituted-tetrahydroisoquinoline ring compounds (amino-substituted-TIQ-ring compounds), for testing as potential drug candidates. The acceleration of drug discovery has generated growing demands for efficient synthetic methods to produce therapeutic candidates. Preferably the methods are suitable for use in generating combinatorial libraries.

Loevezijn et al., *Tetrahedron Letters*, 39:4737–4740 (1998), teach the synthesis of indolyl diketopiperzine alkaloids using a hydroxyethyl functionalized polystyrene resin. Loevezijn et al. disclose loading the resin with L-tryptophan, followed by condensation with an aldehyde or ketone. Loevezijn et al. further disclose that the resulting secondary amine is coupled with a protected amino acid, deprotected and simultaneously cyclized and cleaved. Fantauzzi et al., *Tetrahedron Letters*, 39:1291–1294 (1998), teach the synthesis of tetrahydro-β-carboline-3-carboxamides and tetrahydro-β-carboline-2,3-bis-lactams using a 4-hydroxythiolphenol-linked resin. Fantauzzi et al. disclose acylation of the resin with protected-tryptophan followed by deprotection and cyclization with aldehydes provided tetrahydro-β-carbolines. Fantauzzi et al. further disclose cleavage with primary amines provided the amides, while acylation at the carboline 2-positions with protected amino acids followed by deprotection and neutralization resulted in intramolecular cyclization and cleavage to provide bis-lactams.

Szardenings et al., U.S. Pat. No. 5,817,751, teach methods for the synthesis of diketopiperazine and diketomorpholine derivatives. Szardenings et al. disclose that the methods include providing a first amino acid derivative on a solid support, and combining an aldehyde or ketone, an isocyanide, and a free protected amino acid or an α-hydroxy acid with the first amino acid derivative. The resulting precursor is the cyclized. Schudok, U.S. Pat. No. 5,962,471, teaches substituted 6- and 7-amino-tetrahydroisoquinoline-carboxylic acids suitable for therapy of disorders involving increased activity of matrix-degrading metalloproteinases. Schudok teaches that methods of synthesizing such compounds include the nitration of tetrahydroisoquinoline; acylation with carbonyl or sulfonyl chloride, carboxylic or sulfonic imidazolides, chloroformic acid esters, active esters or anhydrides; treatment with an amino acid, carboxylic acid, aldehyde or substituted guanidine; or alkylation.

There is a need for facile and efficient methods for the synthesis of amino-substituted-TIQ-ring compounds. It is desirable that the methods conveniently produce combinatorial libraries of compounds.

SUMMARY OF THE INVENTION

It is therefore an object of the invention to provide novel methods of preparing amino-tetrahydroisoquinoline ring compounds, particularly amino-substituted-tetrahydroisoquinoline ring compounds such as amino-substituted-tetrahydroisoquinoline-diketopiperazines (amino-substituted-TIQ-DKPs) and amino-substituted-tetrahydroisoquinoline-benzodiazepines (amino-substituted-TIQ-BDAs). It is also an object of the invention to provide novel methods of preparing combinatorial libraries of amino-substituted-tetrahydroisoquinoline ring compounds.

In accordance with one aspect of the invention, there are provided methods of preparing an amino-substituted-tetrahydroisoquinoline ring compound comprising the steps of providing a support-bound amino-substituted-tetrahydroisoquinoline-carboxylic acid in the form of a carboxylate having the structure:

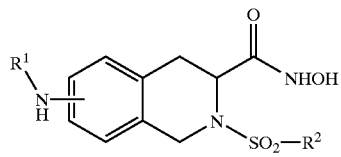

wherein W represents a solid support and $R^1$ is alkyl, aryl, heterocyclic moiety, amide, sulfonamide, urea, thiourea, or alcohol; forming a support-bound intermediate by reacting the support-bound amino-substituted-tetrahydroisoquinoline-carboxylate with a reagent; and cyclizatively cleaving the support-bound intermediate to form the amino-substituted-tetrahydroisoquinoline ring compound. The reagent is selected from the group consisting of (i) isocyanates having the structure $R^3NCO$ wherein $R^3$ is an alkyl or aryl, (ii) thioisocyanates having the structure R4NCS wherein $R^4$ is an alkyl or aryl, (iii) protected non-cyclic amino acids having the structure:

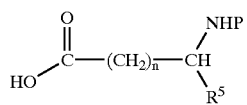

wherein P is a protecting group, n is from 0 to 1, and $R^5$ is the side chain of an amino acid, (iv) protected cyclic amino acids having the structure:

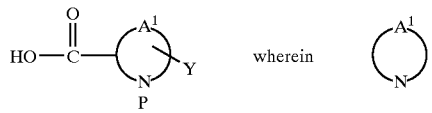

represents a heterocycle, P is a protecting group, and Y is $NO_2$, NHP, OP, or SP, and (v) protected cyclic amino acids having the structure:

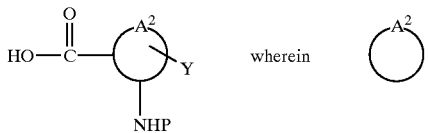 wherein 

represents a heterocycle, aryl, or hydrocarbocycle, P is a protecting group, and Y is $NO_2$, NHP, OP, or SP.

In accordance with another aspect of the invention there are provided methods of preparing an amino-substituted-tetrahydroisoquinoline-diketopiperazine by reacting the support-bound amino-substituted-tetrahydroisoquinoline-carboxylate with the protected cyclic amino acid (iv).

In accordance with yet another aspect of the invention there are provided methods of preparing an amino-substituted-tetrahydroisoquinoline-diketopiperazine by forming a support-bound intermediate having a nitro group and a protecting group by reacting the support-bound amino-substituted-tetrahydroisoquinoline-carboxylate with an amino-protected nitro-substituted-tetrahydroisoquinoline carboxylic acid; reducing the nitro group of the support-bound intermediate; reacting the support-bound intermediate with an aldehyde; removing the protecting group; and cyclizatively cleaving the support-bound intermediate to form amino-substituted-tetrahydroisoquinoline-diketopiperazine.

In accordance with one aspect of the invention there are provided methods of preparing an amino-substituted-tetrahydroisoquinoline-benzodiazepine by reacting the support-bound amino-substituted-tetrahydroisoquinoline-carboxylate with the protected cyclic amino acid (v).

In accordance with yet another aspect of the invention there are provided methods of preparing an amino-substituted-tetrahydroisoquinoline-benzodiazepine by forming a support-bound intermediate having a nitro group and a protecting group by reacting the support-bound amino-substituted-tetrahydroisoquinoline carboxylate with an amino-protected nitro-anthranilic acid; reducing the nitro group of the intermediate; reacting the intermediate with an aldehyde; removing the protecting group; and cyclizatively cleaving the support-bound intermediate to form the amino-substituted-tetrahydroisoquinoline-benzodiazepine.

The present invention provides convenient means for preparing amino-substituted-tetrahydroisoquinoline ring compounds and combinatorial libraries thereof. The present invention also provides convenient means for preparing 7-amino-tetrahydroisoquinoline ring compounds and combinational libraries thereof. These and additional objects and advantages will be more fully apparent in view of the following description.

DETAILED DESCRIPTION

As used herein "amino-substituted-tetrahydroisoquinoline ring compounds" refer to compounds which comprise an isoquinoline moiety having a amino-substituted group and at least one additional ring moiety. Preferably the additional ring moiety is fused to the isoquinoline moiety. The amino-substituted-tetrahydroisoquinoline ring compounds include compounds having the structures:

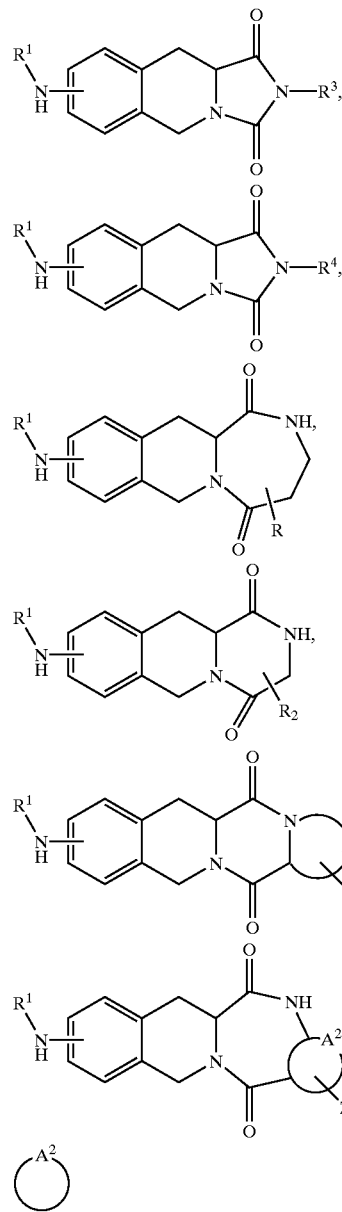

represents a heterocycle, aryl, or hydrocarbocycle;

represents a heterocycle; $R^1$ is alkyl, aryl, heterocyclic moiety, amide, sulfonamide, urea, thiourea, or alcohol and $R^2$ is alkyl, aryl, heterocyclic moiety, amide, sulfonamide, urea, thiourea, hydrogen, or alcohol; $R^3$ and $R^4$ are each independently an alkyl or aryl; n is from 0 to 1; $R^5$ is the side chain of an amino acid and Z is NH, O or S. The amino acid side chain may be selected from the group consisting of side chains of natural and synthetic amino acids.

Examples of suitable amino-substituted-tetrahydroisoquinoline ring compounds include compounds having the structures:

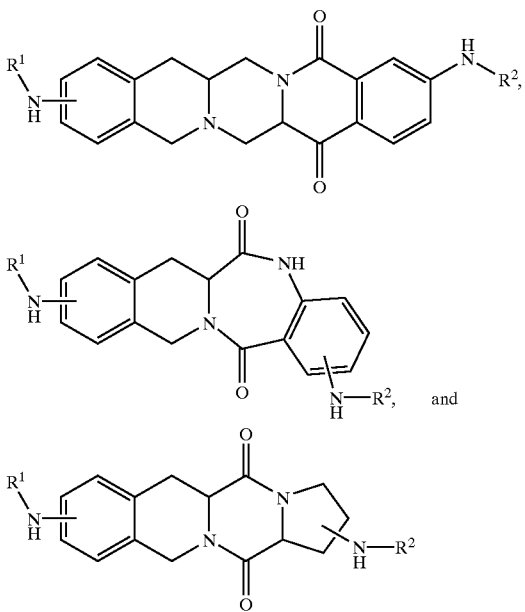

wherein R¹ is alkyl, aryl, heterocyclic moiety, amide, sulfonamide, urea, thiourea, or alcohol and R² is alkyl, aryl, heterocyclic moiety, amide, sulfonamide, urea, thiourea, alcohol or hydrogen. In one embodiment of the invention the amino-substituted-tetrahydroisoquinoline ring compounds include amino-substituted-tetrahydroisoquinoline-diketopiperazines (amino-substituted-TIQ-DKPs) and amino-substituted-tetrahydroisoquinoline-benzodiazepines (amino-substituted-TIQ-BDAs).

As used herein unless specified otherwise, "alkyl" means a hydrocarbon chain which is branched, linear or cyclic, saturated or unsaturated (but not aromatic), substituted or unsubstituted. The term "alkyl" may be used alone or as part of another word where it may be shortened to "alk" (e.g., in alkoxy, alkacyl). Preferred linear alkyls have from one to about twenty carbon atoms, more preferably from one to about ten carbon atoms, more preferably still from one to about six carbon atoms, still more preferably from one to about four carbon atoms; most preferred are methyl or ethyl. Preferred cyclic and branched alkyls have from three to about twenty carbon atoms, more preferably from three to about ten carbon atoms, more preferably still from three to about seven carbon atoms, still more preferably from three to about five carbon atoms. Preferred cyclic alkyls have one hydrocarbon ring, but may have two, three, or more, fused or spirocycle hydrocarbon rings. Preferred alkyls are unsaturated with from one to about three double or triple bonds, preferably double bonds; more preferably they are mono-unsaturated with one double bond. Still more preferred alkyls are saturated. Saturated alkyls are referred to herein as "alkanyl". Alkyls unsaturated only with one or more double bonds (no triple bonds) are referred to herein as "alkanyl". Alkyls unsaturated with one or more triple bonds are referred to herein as "alkanyl". Preferred substituents of alkyls include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, sulfo, alkylsulfo, arylsulfo, sulfino, alkylsulfino, arylsulfino, phospho, alkylphospho, arylphospho, phosphino, alkylphosphino, arylphosphino, nitro, and cyano. Substituents of cycloalkyls also include cycloalkyl, aryl and heterocyclic rings which are fused or spirocycle with the initial cycloalkyl. Unsubstituted alkyls are preferred. An alkyl is bonded to another moiety at the "attaching carbon" of the alkyl. As used herein, "primary alkyl" means that the attaching carbon of the alkyl has two or three hydrogens bonded to it; "secondary alkyl" means that the attaching carbon has one hydrogen bonded to it; and "tertiary alkyl" means that the attaching carbon has no hydrogens bonded to it.

As used herein, "heteroatom" means an atom other than carbon, preferably a nitrogen, oxygen, or sulfur atom.

As used herein, "alkylene" means an alkyl which connects two other moieties, "heteroalkylene" means an alkylene having one or more heteroatoms in the connecting chain.

As used herein unless specified otherwise, "aryl" means an aromatic hydrocarbon ring (or fused rings) which is substituted or unsubstituted. The term "aryl" may be used alone or as part of another word (e.g., in aryloxy, arylacyl). Preferred aryls have from six to about fourteen, preferably to about ten, carbon atoms in the aromatic ring(s), and a total of from about six to about twenty, preferably to about twelve, carbon atoms. Preferred aryls are phenyl or naphthyl; most preferred is phenyl (Ph). Preferred substituents of aryls include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, sulfo, alkylsulfo, arylsulfo, sulfino, alkylsulfino, arylsulfino, phospho, alkylphospho, arylphospho, phosphino, alkylphosphino, arylphosphino, nitro, and cyano. Substituents of aryls also include cycloalkyl and heterocyclic rings which are fused with the aryl ring or rings. Also, unsubstituted aryls are preferred.

As used herein unless specified otherwise, "heterocycle" or "heterocyclic" means a saturated, unsaturated or aromatic cyclic hydrocarbon ring (or fused rings) with one or more heteroatoms in the hydrocarbon ring(s). Preferred heterocycles have from one to about six heteroatoms in the ring(s), more preferably one or two or three heteroatoms in the ring(s). Preferred heterocycles have from three to about fourteen, preferably to about ten, carbon plus heteroatoms in the ring(s), more preferably from three to about seven, more preferably still five or six, carbon plus heteroatoms in the rings(s); and a total of from three to about twenty carbon plus heteroatoms, more preferably from three to about ten, more preferably still five or six, carbon plus heteroatoms. Preferred heterocycles have one ring, but may have two, three, or more, fused rings. More preferred heterocyclic rings include those which are one ring with 5 or 6 carbon plus heteroatoms in the ring with no more than three ring heteroatoms, no more than two of which are O and S. Still more preferred are such 5- or 6-ring atom heterocycles with one or two ring atoms being O or S and the others being C; or with one, two or three ring atoms being N and the others being C. Such preferred 5-or 6-ring atom heterocycles are preferably saturated, unsaturated with one or two double bonds, or aromatic. Such preferred 5- or 6-ring atom heterocycles are preferably a single ring; or fused with a 3- to 6-ring atom hydrocarbon ring which is saturated, unsaturated with one double bond, or aromatic (phenyl); or fused with another such 5- or 6-ring atom heterocyclic ring. Heterocycles are unsubstituted or substituted. Preferred heterocycle substituents are the same as for alkyl.

As used herein, "strong base" means an inorganic hydroxide base, alkyl-alkali metal (e.g., n-butyllithium), alkali metal hydride (e.g., sodium hydride), alkoxide salt (e.g., sodium methoxide), alkali metal amide (e.g., lithium diisopropyl amide), and the like. As used herein, "substantial amount" means a sufficient amount of a specified material such that it effects a subject invention process in a measurable way. As used herein, "substantially free" means a product or other material has less than about 10%, preferably less than about 5%, more preferably less than about 2%, more preferably still less than about 1% of the indicated compound.

As used herein, "non-protic solvent" means a solvent that does not dissociate to provide a substantial and measurable proton concentration, and "non-oxidizing solvent" means a solvent that does not have substantial oxidizing potential. Protic solvents include, for example, water, methanol, ethanol, dimethylformamide and the like. Oxidizing solvents include, for example, dimethylsulfoxide, and the like.

As used herein "combinatorial library" of compounds means a mixture of related compounds or a group of individual compounds, made substantially simultaneously by substantially the same process using a mixture of or individual related reactants to obtain related compounds. The combinatorial library may be formed by separating a support-bound reactant into two or more portions and reacting the respective portions with different reactants. Alternatively, the combinatorial library may be formed by reacting a support-bound reactant with a mixture of reactants. Finally, the combinatorial library may be formed by a method which employs a combination of these processes.

As used herein "protecting group" refers to a moiety attached to a functional group, such as an amine, to prevent an undesired reaction. Preferably the protecting group may be easily removed after protection of the functional group is no longer required. Suitable protecting groups include t-butyloxycarbonyl (Boc), 9-fluorenylmethoxycarbonyl (Fmoc), benzyloxycarbonyl, allyloxycarbonyl, and (trimethylsilyl)ethoxycarbonyl.

Synthetic methods in accordance with the present invention utilize an amino-tetrahydroisoquinoline-carboxylic acid (amino-substituted-TIQ-carboxylic acid) attached to a solid support, preferably a resin, more preferably a polyester resin, a polyolefin resin such as polyethylene, or a polyvinyl resin such as polyester. Preferred resins include modified polyester resins.

The support-bound amino-substituted-TIQ-carboxylic acid may be formed in any suitable manner. For example, support-bound amino-substituted-TIQ-carboxylic acid may be formed by providing a nitro-substituted-tetrahydroisoquinoline carboxylic acid (nitro-substituted-TIQ-carboxylic acid) with a protecting group to form an orthogonally protected nitro-substituted-TIQ-carboxylic acid; attaching the orthogonally protected nitro-substituted-TIQ-carboxylic acid to the solid support, thereby forming a carboxylate; and reducing the nitro group to form the orthogonally protected amino-substituted-TIQ-carboxylate. In another embodiment, tetrahydroisoquinoline carboxylic acid may be first bound to the support, and then may be nitrated in the 4-, 5-, 6- or 7-position followed by reduction of the nitro group to an amino.

The TIQ-carboxylic acid or carboxylate may be nitrated by any suitable manner, such as treatment with sulfuric acid and potassium nitrate or with nitronium tetrafluoroborate and acetonitrile, and the nitro compound may be reduced by any suitable manner, such as hydrogenation over a metal catalyst, for example, a palladium catalyst or $SnCl_2$ in dimethyl-formamide. The ring nitrogen may be protected and deprotected in any suitable manner. A suitable protection method comprises reaction the TIQ-carboxylic acid with di-t-butyl bicarbonate, while a suitable de-protection method comprises treatment with a strong acid such as trifluoroacetic. The protecting group may selected from the group consisting of t-butyloxycarbonyl (Boc), 9-fluorenylmethoxycarbonyl (Fmoc), benzyloxycarbonyl, allyloxycarbonyl, (trimethylsilyl)ethoxycarbonyl and mixtures thereof.

Generally the TIQ-acid is attached to the solid support by any suitable manner. In one embodiment the TIQ-carboxylic acid is attached to the solid support through the acid moiety, more particularly through reaction of the support with the hydroxyl segment of the carboxylic acid moiety, to form a carboxylate.

In a further embodiment, the amino-substituted group of the support-bound amino-substituted-TIQ-carboxylate is substituted. While not being bound by theory, the preparation of the support-bound substituted amino-substituted-TIQ-carboxylic acid occurs as set forth in Reaction Sequence 1 below:

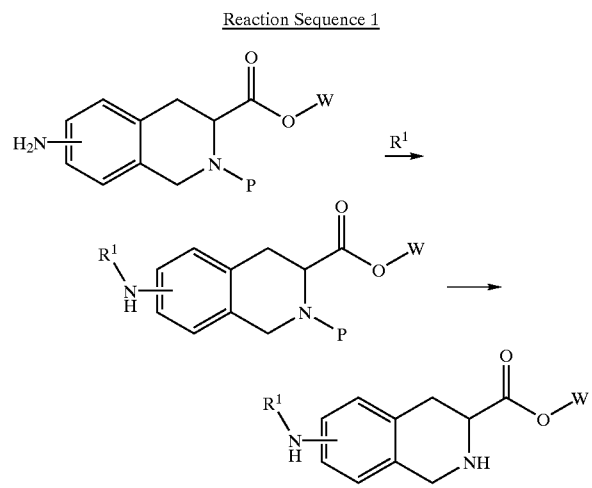

Reaction Sequence 1 wherein W represents a solid support and P represents a protecting group.

Suitable $R^1$ groups include amides, sulfonamides, ureas, thioureas, alcohols, alkyls, aryls, heterocyclic moieties and mixtures thereof. Any desired moieties may be used to form the $R^1$ group, suitable moieties include acyl halides; carboxylic acids, including amino acids; sulfonyl chlorides; isocyanates; isothiocyanates; epoxides; halides, including alkyl halides and aryl halides; aldehydes; and mixtures thereof. As used herein "amino acids" is intended to include N-protected amino acids.

In one embodiment, the $R^1$ group is an amide formed by reacting the amino-substituted-TIQ-carboxylate with an acyl chloride, generally in the presence of N,N-diisopropylethylamine (DIEPA) and dichloroethane. The reaction may occur at room temperature for period of time of about 12 hours. In another embodiment the amide is formed by activating a carboxylic acid in solution using (benzotriazol-1-yloxy)-tris(pyrrolidino)phosphonium hexafluorophosphate (PyBOP) in dimethylformamide (DMF), and adding the solution to the amino-substituted-TIQ-carboxylate. The reaction may occur at room temperature for period of time of from about 1 to about 2 hours. The carboxylic acid may be an amino acid, such as a N-protected amino acid.

In one embodiment, the $R^1$ group is a sulfonamide formed by reacting the amino-substituted-TIQ-carboxylate with a sulfonyl chloride, generally in the presence of 4-(dimethylamino)pyridine (DMAP) and pyridine. In a further embodiment, the step of forming the sulfonamide comprises reacting the amino-substituted-TIQ-carboxylate with sulfonyl chloride in the presence of about 1%, by weight, 4-dimethylaminopyridine and pyridine at room temperature for from about 6 to about 12 hours. Generally the mole ratio of amino-substituted-TIQ-carboxylate to sulfonyl chloride is from about 1:2 to about 1:8, preferably from about 1:3 to about 1:5.

In one embodiment, the $R^1$ group is a urea or thiourea formed by reacting the amino-substituted-TIQ-carboxylate with an isocyanate or isothiocyanate, respectively, generally in the presence of NaH in dimethylformamide. In a further embodiment, the amino-substituted-TIQ-carboxylate is reacted with an isocyanate or isothiocyanate in the presence of about 1%, by weight NaH in dimethylformamide at room temperature for about 12 hours. Generally the mole ratio of amino-substituted-TIQ-carboxylate to urea or thiourea is from about 1:3 to about 1:5.

In one embodiment, the $R^1$ group is an alcohol formed by reacting the amino-substituted-TIQ-carboxylate with an epoxide, generally in the presence of an alcohol solvent. In a further embodiment, the reaction occurs at a temperature of about 80° C. and for a time period of about 16 hours. In one embodiment the alcohol solvent is a mixture of ethanol and isopropanol, preferably in a volume ratio of about 1:1 ethanol:isopropanol. Generally the mole ratio of amino-substituted-TIQ-carboxylate to epoxide is from about 1:3 to about 1:5.

In one embodiment, the $R^1$ group is an alkyl formed by reacting the amino-substituted-TIQ-carboxylate with an alkyl halide, preferably an alkyl bromide. Generally the step of forming the alkyl substituent comprises reacting the amino-TIQ-substituted-carboxylate with an alkyl halide in the presence of $Bu_4NHSO_4$ and $Na_2CO_3$. In a further embodiment, the step comprises reacting the amino-substituted-TIQ-carboxylate with an alkyl bromide in a solution comprising about 2%, by weight, $Bu_4NHSO_4$, about 5%, by weight, $Na_2CO_3$ and toluene at a temperature of about 70° C. for a period of time of about 8 hours. Generally the mole ratio of amino-substituted-TIQ-carboxylate to alkyl halide is from about 1:2 to about 1:4.

In one embodiment, the $R^1$ group is an alkyl formed by reductive alkylation. The amino-substituted-TIQ-carboxylate may be reacted with an aldehyde in the presence of a borane/pyridine complex. In a further embodiment, the alkylation comprises reacting the amino-substituted-TIQ-carboxylate with an aldehyde in the presence of a borane/pyridine complex in a mixing solvent comprising ethanol and dimethyl formamide, more preferably the mixing solvent comprises ethanol and dimethyl formamide in a ethanol:dimethyl formamide weight ratio of about 3:1. Generally the mole ratio of amino-substituted-TIQ-carboxylate to aldehyde is from about 1:2 to about 1:4. The borane/pyridine complex is generally prepared by a commercially available reagent from Aldrich.

The amino-substituted-TIQ-ring compounds are prepared by reacting the support-bound amino-substituted-tetrahydroisoquinoline-carboxylic acid with a reagent selected from the group consisting of (i) isocyanates having the structure $R^3NCO$ wherein $R^3$ is an alkyl or aryl, (ii) thioisocyanates having the structure $R^4NCS$ wherein $R^4$ is an alkyl or aryl, (iii) protected non-cyclic amino acids having the structure:

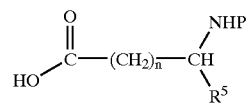

wherein P is a protecting group, n is from 0 to 1, and $R^5$ is the side chain of an amino acid, such as natural and synthetic amino acids, (iv) protected cyclic amino acids having the structure:

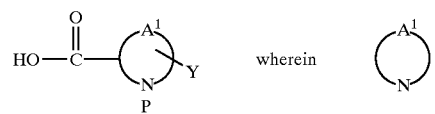

represents a heterocycle, P is a protecting group, and Y is $NO_2$, NHP, OP, or SP, and (v) protected cyclic amino acids having the structure:

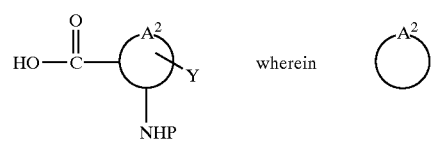

represents a heterocycle, aryl, or hydrocarbocycle, P is a protecting group, and Y is $NO_2$, NHP, OP, or SP. The reaction between the support-bound amino-substituted-TIQ-carboxylate and the reagent forms a support-bound intermediate which is then cyclizatively cleaved from the support to form the amino-substituted-TIQ ring compound. While not being bound by theory, the amino-substituted-TIQ ring compounds are believed to be formed as set forth below in Reaction Sequence 2.

Reaction Sequence 2

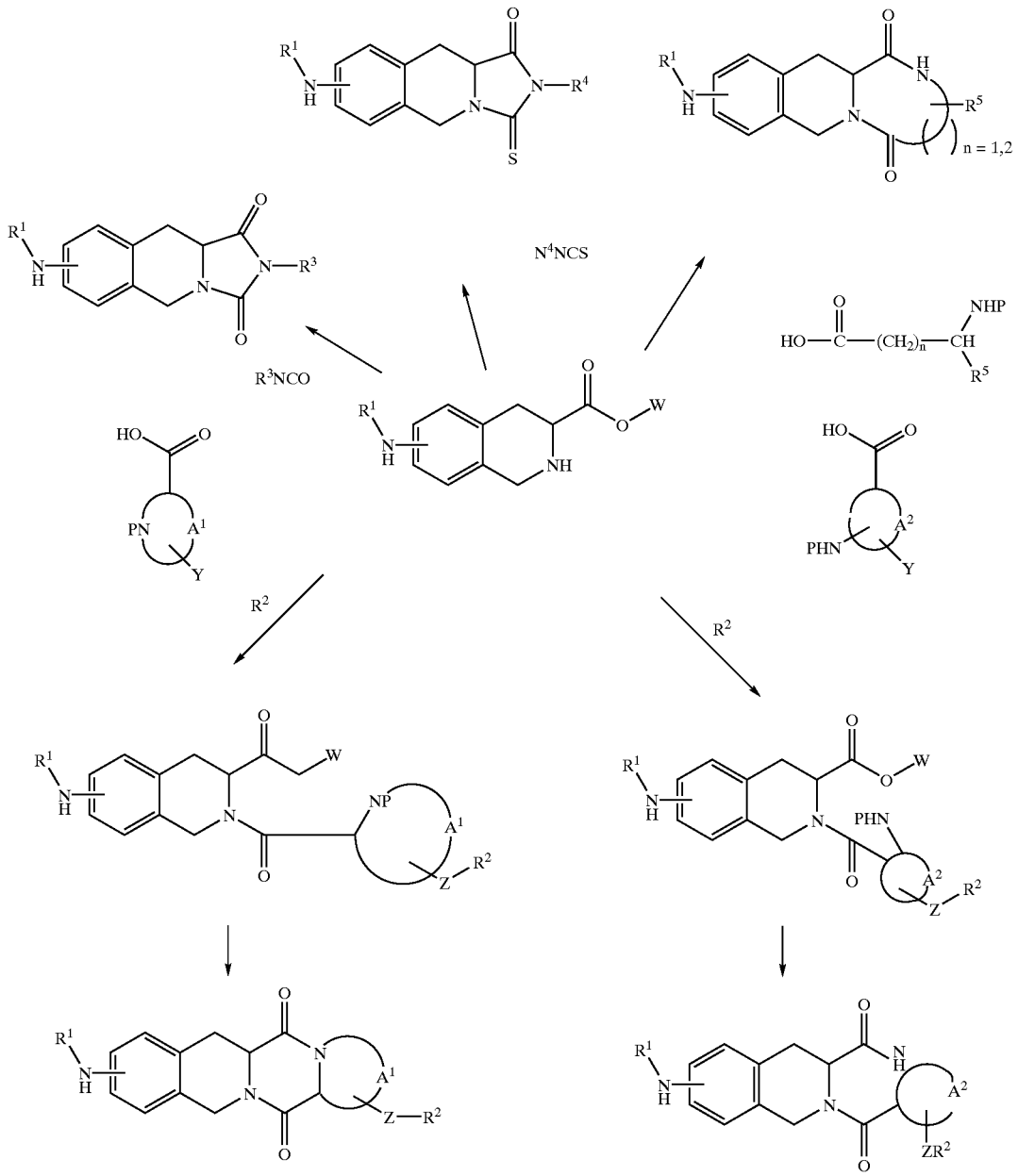

wherein W represents a solid support; $R^1$ is alkyl, aryl, heterocyclic moiety, amide, sulfonamide, urea, thiourea, or alcohol, and $R^2$ is alkyl, aryl, heterocyclic moiety, amide, sulfonamide, urea, thiourea, alcohol, or hydrogen; $R^3$ and $R^4$ are each independently an alkyl or aryl; $R^5$ is the side chain of an amino acid selected from the group consisting of natural and synthetic amino acids; P is a protecting group; n is from 0 to 1;

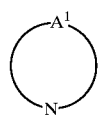

represents a heterocycle;

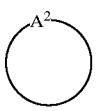

represents a heterocycle, aryl, or hydrocarbocycle; Y is $NO_2$, NHP, OP, or SP; and Z is NH, O or S.

The step of reacting the support-bound amino-substituted-TIQ-carboxylic acid with the reactant occurs for a sufficient time and at a sufficient temperature for the reaction to occur. Generally, when the reactant is an isocyanate or an thioisocyante the reaction occurs in the presence of a solvent, preferably a non-protic and non-oxidizing solvent such as CH$_2$Cl$_2$. The reaction between the support-bound amino-substituted-TIQ-carboxylic acid and the isocyanate or thioisocyante generally occurs at room temperature for a period of time from about 4 to about 12 hours, preferably about 6 hours.

When the substrate is a protected amino acid, such as the protected non-cyclic amino acids or protected cyclic amino acids, the acid is generally first activated prior to reacting with the support-bound amino-substituted-TIQ-carboxylic acid. One suitable activation method comprises treating the acid with (benzotirazol-1-yloxy)-tris(pyrrolidino) phosphonium hexafluorophosphate (PyBOP) and N,N-diisopropylethylamine (DIEPA). Generally, the activation occurs in the presence of a solvent such as dimethylfomamide (DMF) at room temperature of from about 1 to 2 hours, preferably about one hour. The activated acid is then added to the support-bound amino-substituted-TIQ-carboxylic acid for the coupling. The coupling reaction is generally carried out in the presence of a solvent, such as DMF, at room temperature for a period of time of from about 6 to about 24 hours, preferably about 12 hours.

The protected amino group is then deprotected by any suitable means. Suitable means of removing protecting groups such as BOC is treatment with trifluoroacetic acid (TFA) in a solvent such as CH$_2$Cl$_2$, followed by heating with acetic acid in a solvent such as isopropanol. In one embodiment the protected amino group is deprotected by treatment with 25% TFA in CH$_2$Cl$_2$, followed by heating at a temperature from about 60 to about 90° C., preferably about 80° C., in 20% acetic acid in isopropanol for a period of time from about 8 to 24 hours, preferably about 12 hours.

In one embodiment of the invention, the support-bound amino-substituted-TIQ-carboxylic acid is reacted with a protected cyclic amino acid, and the resulting intermediate is provided with a substituent on the cyclic moiety provided by the cyclic amino acid. The resulting amino-substituted-TIQ ring compounds have the structure:

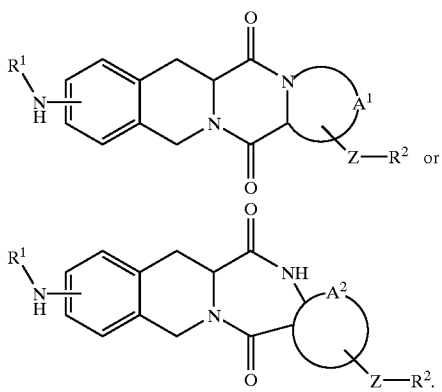

Suitable R$^2$ groups include amides, sulfonamides, ureas, hydrogen, thioureas, alcohols, alkyls, aryls, heterocyclic moieties and mixtures thereof. Any desired moieties may be used to form the R$^2$ group, suitable moieties include acyl halides; carboxylic acids, including amino acids; sulfonyl chlorides; isocyanates; isothiocyanates; epoxides; halides, including alkyl halides and aryl halides; aldehydes; and mixtures thereof. As used herein "amino acids" is intended to include N-protected amino acids. The reaction step to provide R$^2$ is omitted if R$^2$ is hydrogen.

In one embodiment, the R$^2$ group is an amide formed by reacting the amino-substituted-TIQ-carboxylate with an acyl chloride, generally in the presence of N,N-diisopropylethylamine (DIEPA) and dichloroethane. The reaction may occur at room temperature for period of time of about 12 hours.

In another embodiment, the amide is formed by activating a carboxylic acid in solution using (benzotriazol-1-yloxy)-tris(pyrrolidino)phosphonium hexafluorophosphate (PyBOP) in dimethylformamide (DMF), and adding the solution to the amino-substituted-TIQ-carboxylate. The reaction may occur at room temperature for period of time of from about 1 to about 2 hours. The carboxylic acid may be an amino acid, such as a N-protected amino acid.

In one embodiment, the R$^2$ group is a sulfonamide formed by reacting the amino-substituted-TIQ-carboxylate with a sulfonyl chloride, generally in the presence of 4-(dimethylamino)pyridine (DMAP) and pyridine. In a further embodiment, the step of forming the sulfonamide comprises reacting the amino-substituted-TIQ-carboxylate with a sulfonyl chloride in the presence of about 1%, by weight, 4-dimethylaminopyridine and pyridine at room temperature for from about 6 to about 12 hours. Generally the mole ratio of amino-substituted-TIQ-carboxylate to sulfonyl chloride is from about 1:2 to about 1:8, preferably from about 1:3 to about 1:5.

In one embodiment, the R$^2$ group is a urea or thiourea formed by reacting the amino-substituted-TIQ-carboxylate with an isocyanate or isothiocyanate, respectively, generally in the presence of NaH in dimethylformamide. In a further embodiment, the amino-substituted-TIQ-carboxylate is reacted with an isocyanate or isothiocyanate in the presence of about 1%, by weight, NaH in dimethylformamide at room temperature for about 12 hours. Generally the mole ratio of amino-substituted-TIQ-carboxylate to isocyanate or isothiocyanate is from about 1:3 to about 1:5.

In one embodiment, the R$^2$ group is an amino alcohol formed by reacting the amino-substituted-TIQ-carboxylate with an epoxide, generally in the presence of an alcohol solvent. In a further embodiment, the reaction occurs at a temperature of about 80° C. and for a time period of about 16 hours. In one embodiment the alcohol solvent is a mixture of ethanol and isopropanol, preferably in a volume ratio of about 1:1 ethanol:isopropanol. Generally the mole ratio of amino-substituted-TIQ-carboxylate to epoxide is from about 1:3 to about 1:5.

In one embodiment, the R$^2$ group is an alkyl formed by reacting the amino-substituted-TIQ-carboxylate with an alkyl halide, preferably an alkyl bromide. Generally the step of forming the alkyl substituent comprises reacting the amino-substituted-TIQ-carboxylate with an alkyl halide in the presence of Bu$_4$NHSO$_4$ and Na$_2$CO$_3$. In a further embodiment, the step comprises reacting the amino-substituted-TIQ-carboxylate with an alkyl bromide in a solution comprising about 2%, by weight, Bu$_4$NHSO$_4$, about 5%, by weight, Na$_2$CO$_3$ and toluene at a temperature of about 70° C. for a period of time of about 8 hours. Generally the mole ratio of amino-substituted-TIQ-carboxylate to alkyl halide is from about 1:2 to about 1:4.

In one embodiment, the R$^2$ group is an alkyl formed by reductive alkylation. The amino-substituted-TIQcarboxylate may be reacted with an aldehyde in the presence of a borane/pyridine complex. In a further embodiment, the alkylation comprises reacting the amino-substituted-TIQ-carboxylate with an aldehyde in the presence of a borane/pyridine complex in a mixing solvent comprising ethanol and dimethyl formamide, more preferably the mixing solvent comprises ethanol and dimethyl formamide in a ethanol:dimethyl formamide weight ratio of about 3:1. Generally the mole ratio of amino-substituted-TIQ-carboxylate to aldehyde is from about 1:2 to about 1:4. The borane/pyridine complex is a commercially available reagent from Aldrich.

The support-bound intermediate is cyclizatively cleaved from the support. In some embodiments, such as when the reactant is an isocyanate, thioisocyanate, or protected non-cyclic amino acid, the cleavage occurs during the reaction of the support-bound amino-substituted-TIQ-carboxylate with the reactant, while in other embodiments, (a protected cyclic amino acid), the cleavage occurs after the initial reaction of the reactant, 1, with the support-bound amino-substituted-TIQ-carboxylate. As used herein, "cyclizatively cleaving" refers to a process wherein the reactant is cyclized and cleaved from the solid support simultaneously.

In one embodiment, the reactant is a protected cyclic amino acid. The support-bound intermediate formed by reacting the protected cyclic amino acid and the support-bound amino-substituted-TIQ-carboxylic acid is cleaved by deprotection of the protected amino group followed by heating in acid. In one embodiment, the protecting group is removed by treatment with trifluoroacetic acid in $CH_2Cl_2$, followed by heating with acetic acid in isopropanol. In a preferred embodiment, the support-bound intermediate is deprotected with 25% TFA in $CH_2Cl_2$, followed by heating at about 80° C. in 20%, by weight, acetic acid in isopropanol for a period of time from about 8 to about 24 hours, preferably about 12 hours.

Generally any amino-substituted-TIQ-carboxylic acid which has not reacted with the reagent will remain attached to the support during the cyclizative cleavage, while the desired product is cleaved. If desired, the resulting amino-substituted-TIQ-ring compound may be further isolated and/or purified by any art recognized method, such as solvent extraction and recrystallization, thin layer chromatography, or high pressure liquid chromatography (HPLC).

Combinatorial libraries of amino-substituted-tetrahydroisoquinoline ring compounds may be prepared using methods in accordance with the present invention. A suitable method of preparing a combinatorial library comprises the steps of providing a support-bound amino-substituted-tetrahydroisoquinoline-carboxylic acid in the form of a carboxylate having the structure:

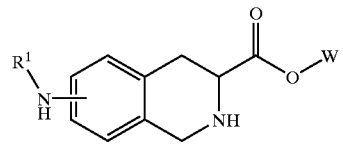

wherein W represents a solid support and $R^1$ is alkyl, aryl, heterocyclic moiety, amide, sulfonamide, urea, thiourea, or alcohol. The support-bound amino-substituted-TIQ-carboxylic acid may then be partitioned into a first portion of support-bound amino-substituted-TIQ-carboxylate and a second portion of support-bound amino-substituted-TIQ-carboxylate; and a first support-bound intermediate is formed by reacting the first portion of support-bound amino-substituted-TIQ-carboxylate with a first reagent and a second support-bound intermediate is formed by reacting the second portion of support-bound amino-substituted-tetrahydroisoquinoline-carboxylate with a second reagent.

The first and second support-bound intermediates are then cyclizatively cleaved to form first and second amino-substituted-tetrahydroisoquinoline ring compounds, respectively. The first and second reagents are selected from the group consisting of reagents (i), (ii), (iii), (iv) and (v) as described above.

In one embodiment, when the first and second reagents are both isocyanates, the first reagent is a different isocyanate than the second reagent; when the first and second reagents are both thioisocyanates, the first reagent is a different thioisocyanate than the second reagent; when the first and second reagents are both protected non-cyclic amino acids, the first reagent is a different protected amino acid than the second reagent; and when the first and second reagents are both protected cyclic amino acids, the first reagent is a different protected cyclic amino acid than the second reagent. In another embodiment, the first reagent and the second reagent are the same protected cyclic amino acid, however the first and second support-bound intermediates are provided with different $R^2$ groups prior to cyclizative cleavage.

EXAMPLE 1

A substituted 7-amino-tetrahydroisoquinoline ring compound in accordance with the invention is prepared as set forth in Reaction Sequence 3, below:

Reaction Sequence 3

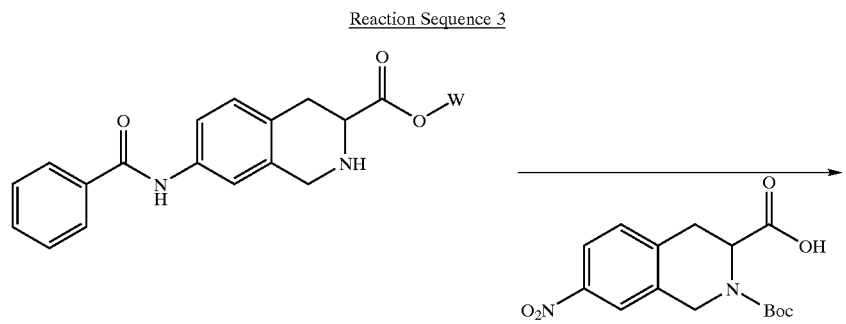

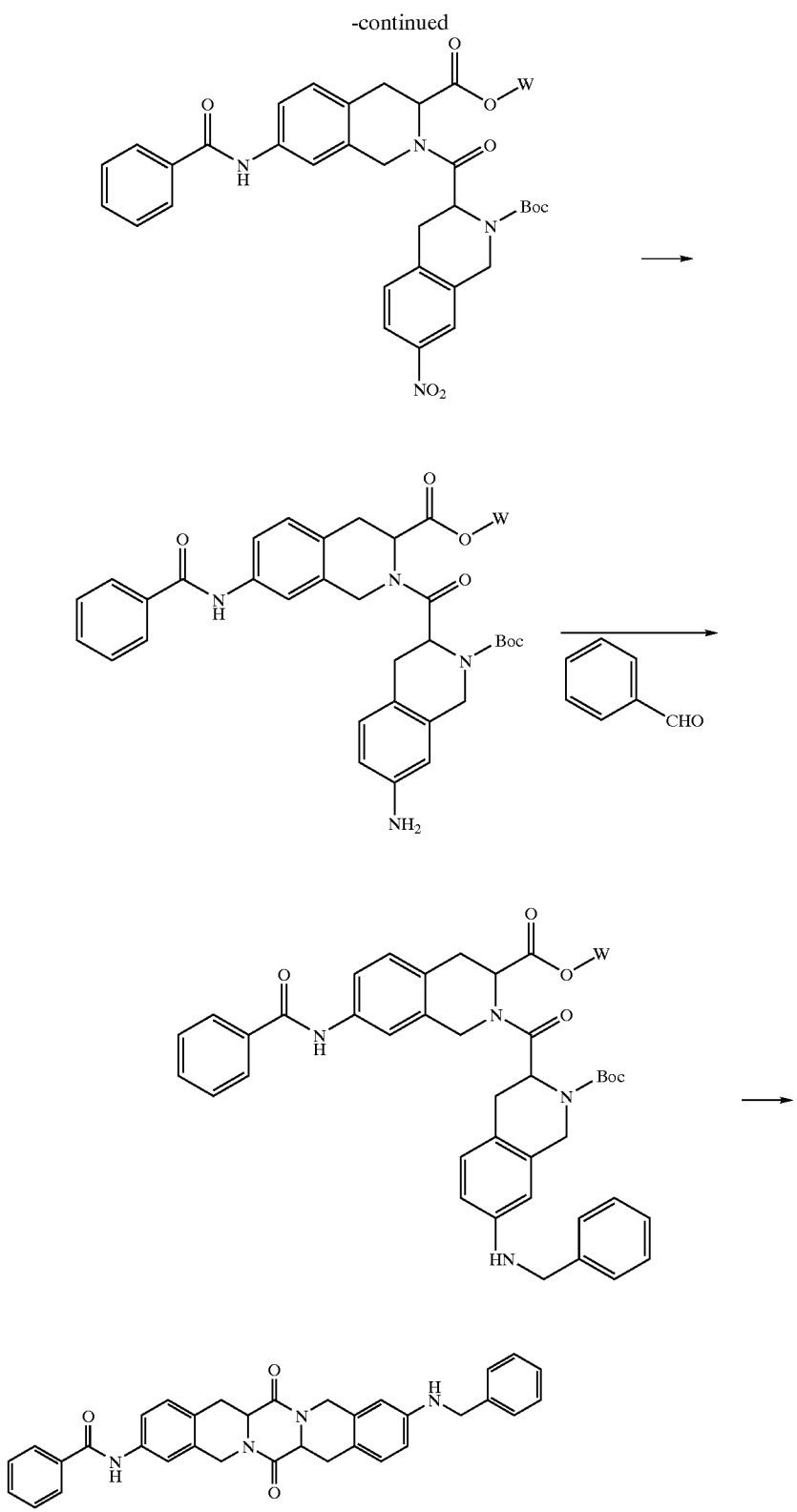

wherein W represents a solid support and Boc represents the protecting agent t-butyloxycarbonyl. The support bound substituted 7-amino-TIQ-carboxylic acid is activated using PyBOP. The nitro group provided by the 7-nitro-TIQ-carboxylic acid is reduced to provide a point of attachment of a second substituent. Reductive alkylation using benzaldehyde in the presence of a boran-pyridine complex yields an intermediate. The BOC group is removed and the intermediate is cleaved by the resin to form the 7-amino-TIQ-diketopiperazine.

EXAMPLE 2

A substituted-7-amino-TIQ ring compound is prepared in accordance with Reaction Sequence 4, below, wherein W represents a solid support.

Reaction Sequence 4

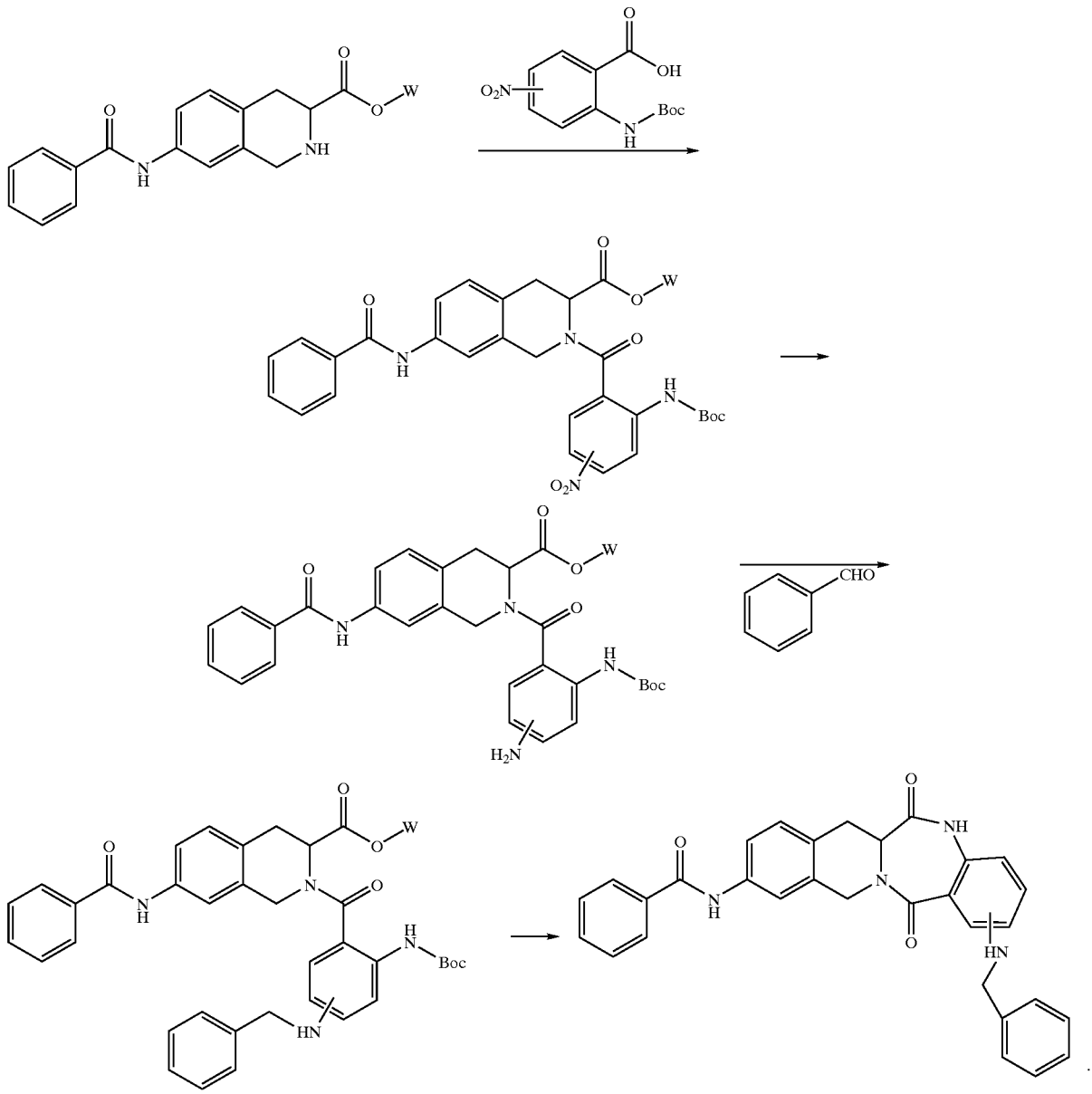

The support-bound substituted-7-amino-TIQ-carboxylic acid is coupled with a Boc-protected-nitro-anthranilic acid which is activated using PyBOP. Reduction of the nitro group provided by the protected-nitro-anthranilic acid provides a point of attachment. Reductive alkylation using benzaldehyde in the presence of borane/pyridine complex yields the intermediate, which is cleaved to provide the desired 7-amino-TIQ-benzodiazepine.

Throughout the specification, all percentages and ratios are by weight unless specifically indicated otherwise. Additional embodiments and modifications within the scope of the claimed invention will be apparent to one of ordinary skill in the art. Accordingly, the scope of the present invention shall be considered in the terms of the following claims and is understood not to be limited to the details or the methods described in the specification.

What is claimed:
1. A method of preparing an amino-substituted-tetrahydroisoquinoline ring compound; wherein said compound comprises a structure selected from the group consisting of:

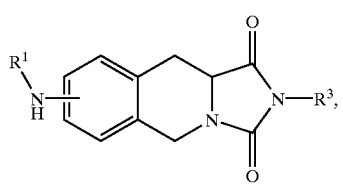

-continued

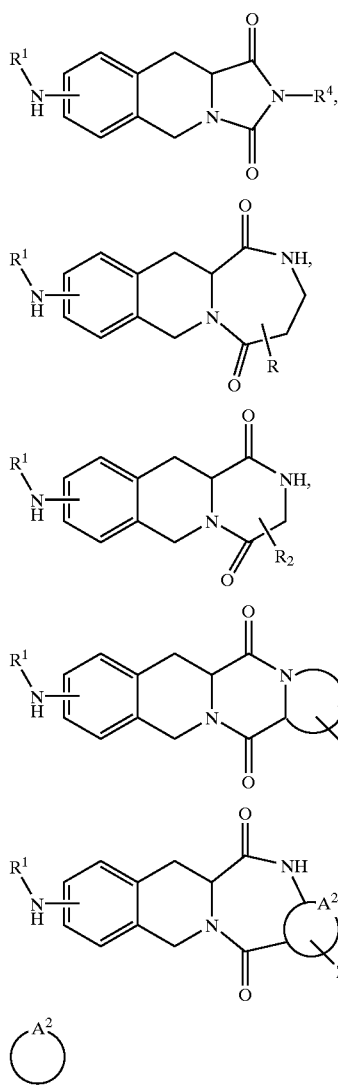

represents a heterocycle, aryl, or hydrocarbocycle;

represents a heterocycle; $R^1$ is alkyl, aryl, heterocyclic moiety, amide, sulfonamide, urea, thiourea, or alcohol and $R^2$ is alkyl, aryl, heterocyclic moiety, amide, sulfonamide, urea, thiourea, hydrogen, or alcohol; $R^3$ and $R^4$ are each independently an alkyl or aryl; n is from 0 to 1; $R^5$ is the side chain of an amino acid and Z is NH, O or S; wherein the amino acid side chain may be selected from the group consisting of side chains of natural and synthetic amino acids;

comprising the steps of (a) providing a support-bound amino-substituted-tetrahydroisoquinoline-carboxylic acid in the form of a carboxylate having the structure:

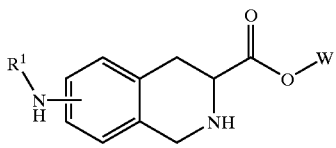

wherein W represents a solid support and $R^1$ is alkyl, aryl, heterocyclic moiety, amide, sulfonamide, urea, thiourea, or alcohol; (b) forming a support-bound intermediate by reacting the support-bound amino-substituted-tetrahydroisoquinoline-carboxylate with a reagent selected from the group consisting, of: (i) isocyanates having the structure $R^3NCO$ wherein $R^3$ is an alkyl or aryl, (ii) thioisocyanates having the structure $R^4NCS$ wherein $R^4$ is an alkyl or aryl, (iii) protected non-cyclic amino acids having the structure:

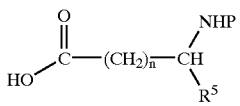

wherein P is a protecting group, n is from 0 to 1, and $R^5$ is the side chain of an amino acid, and (iv) protected cyclic amino acids having the structure:

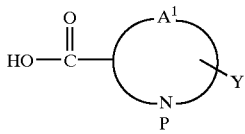

wherein

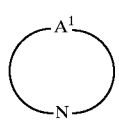

represents a heterocycle, P is a protecting group, and Y is $NO_2$, NHP, OP, or SP, and (v) protected cyclic amino acids having the structure:

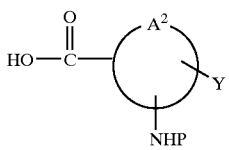

wherein

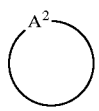

represents a heterocycle, aryl, or hydrocarbocycle, P is a protecting group, and Y is $NO_2$, NHP, OP, or SP; and (c) cyclizatively cleaving the support-bound intermediate to form the amino-substituted-tetrahydroisoquinoline ring compound.

2. A method according to claim 1, wherein step b comprises reacting the support-bound amino-substituted-tetrahydroisoquinoline-carboxylate with a reagent selected from the group consisting of protected nitro-substituted-tetrahydroisoquinoline carboxylic acid, protected nitro-anthranilic acid and mixtures thereof.

3. A method according to claim 1, wherein step b comprises reacting the support-bound amino-substituted-tetrahydroisoquinoline-carboxylate with a reagent selected from the group consisting of isocyanates, thioisocyanates and mixtures thereof at room temperature.

4. A method according to claim 1, wherein step b comprises the steps of: (i) activating an acid with (benzotriazol-1-yloxy)-tris(pyrrolidino)phosphonium hexafluorophosphate and N,N-diisopropylethylamine at room temperature, wherein the acid has a protected amino group and is selected from the group consisting of protected non-cyclic amino acids, protected cyclic amino acids and mixtures thereof; (ii) coupling the acid having a protected amino group and the support-bound amino-substituted-tetrahydroisoquinoline-carboxylate at room temperature to form a support-bound precursor having a protected amino group; and (iii) deprotecting the protected amino group to form the support-bound intermediate.

5. A method according to claim 1, wherein the support-bound amino-substituted-tetrahydroisoquinoline-carboxylic acid is prepared by a process comprising the steps of: (i) providing an amino-substituted-tetrahydroisoquinoline-carboxylic acid with a protecting group to form an orthogonally protected amino-substituted-tetrahydroisoquinoline-carboxylic acid; (ii) attaching the orthogonally protected amino-substituted-tetrahydroisoquinoline-carboxylic acid to a solid support to form a carboxylate; (iii) attaching the $R^1$ group to the amino of the amino-substituted-tetrahydroisoquinoline-carboxylate; and (iv) removing the protecting group from the amino-tetrahydroisoquinoline-substituted-carboxylate.

6. A method according to claim 1, wherein the solid support is a polyethylene resin.

7. A method according to claim 1, wherein the protecting group is t-butoxycarbonyl.

8. A method according to claim 1, wherein step b comprises reacting the support-bound amino-substituted-tetrahydroisoquinoline-carboxylic acid with a reagent selected from the group consisting of protected cyclic amino acids (iv) and protected cyclic amino acids (v) and mixtures thereof; and removing the protecting group; and wherein the method further comprises the step of attaching an $R^2$ group to form a support-bound intermediate selected from the group consisting of:

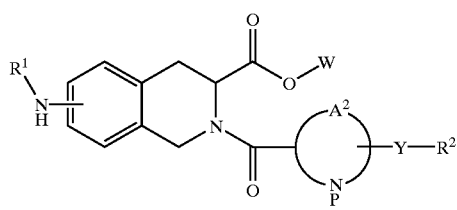

i

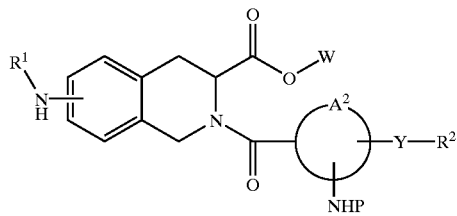

ii and iii. mixtures thereof; wherein $R^2$ is amide, sulfonamide, urea, thiourea, alcohol, alkyl, aryl, hydrogen, or heterocycle; and wherein cyclizatively cleaving the support-bound intermediate produces a amino-substituted-tetrahydroisoquinoline ring compound selected from the group consisting of:

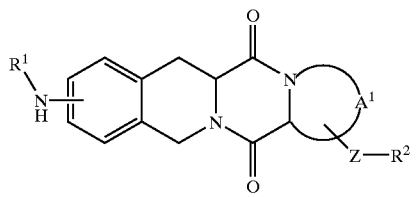

i

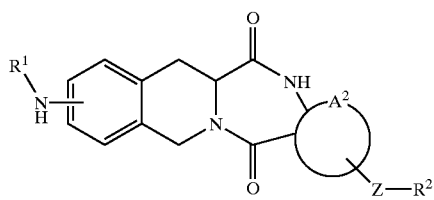

ii and iii. mixtures thereof; wherein Z is NH, O or S.

9. A method according to claim 1, wherein step b comprises reacting the support-bound amino-substituted-tetrahydroisoquinoline-carboxylic acid with a reagent selected from the group consisting of protected cyclic amino acids (iv), protected cyclic amino acids (v), and mixtures thereof; and reducing the $NO_2$; and wherein the method further comprises the step of attaching an $R^2$ group to form a support-bound intermediate selected from the group consisting of:

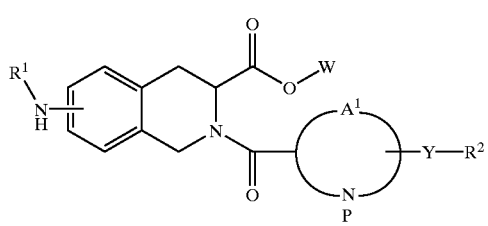

i

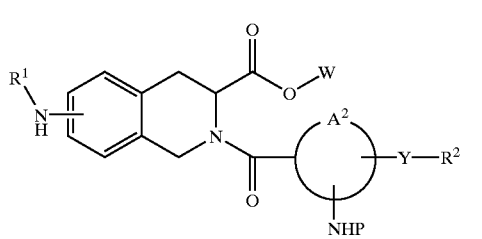

ii and iii. mixtures thereof;

wherein $R^2$ is amide, sulfonamide, urea, thiourea, alcohol, alkyl, aryl, hydrogen, or heterocycle;

and wherein cyclizatively cleaving the support-bound intermediate produces a amino-substituted-tetrahydroisoquinoline ring compound selected from the group consisting of:

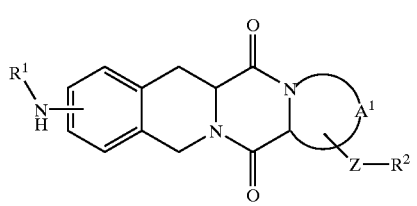

i

-continued

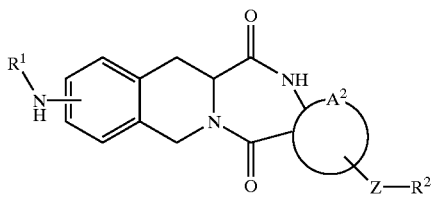

and iii. mixtures thereof, wherein Z is NH, O or S.

10. A method according to claim 1, wherein the amino-substituted-tetrahydroisoquinoline ring compound is a 7-amino-tetrahydroisoqunoline ring compound.

11. A method according to claim 1, wherein the amino-substituted-tetrahydroisoquinoline-diketopiperazine and step b comprises forming a support-bound intermediate by reacting the support-bound amino-substituted-tetrahydroisoquinoline-carboxylic acid with the protected cyclic amino acid (iv).

12. A method according to claim 11, wherein step b occurs in the presence of (benzotriazol-1-yloxy)-tris(pyrrolidino) phosphonium hexafluorophosphate.

13. A method according to claim 11, wherein the amino-substituted-tetrahydroisquinoline-diketopiperazine is 7-amino-tetrahydroisquinoline-diketopiperazine.

14. A method according to claim 11, wherein step b comprises forming a support-bound intermediate having a nitro group and a protecting group by reacting the support-bound amino-substituted-tetrahydroisoquinoline carboxylic acid with an amino-protected nitro-substituted-tetrahydroisoquinoline carboxylic acid; reducing the nitro group of the support-bound intermediate; reacting the support-bound intermediate with a reactant selected from the group consisting of acyl chlorides, solutions comprising a carboxylic acid and a N-protected amino acid, sulfonyl chlorides, isocyanates, isothiocyanates, epoxides, alkyl halides, aldehydes, and mixtures thereof; removing the protecting group.

15. A method according to claim 14, wherein the amino-protected-nitro-tetrahydroisoquinoline carboxylic acid has the structure:

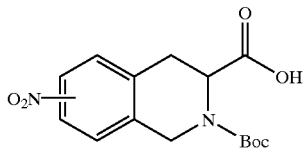

wherein Boc represents t-butyloxycarbonyl.

16. A method according to claim 14, wherein the nitro-substituted-tetrahydroisoquinoline-carboxylic acid is 7-nitro-tetrahydroisoquinoline carboxylic acid.

17. A method according to claim 1, wherein the amino-substituted-tetrahydroisoquinoline ring compound is an amino-substituted tetrahydroisoquinoline-benzodiazepine and wherein step b comprises forming a support-bound intermediate by reacting the amino-substituted-tetrahydroisoquinoline carboxylate with a protected cyclic amino acid (v).

18. A method according to claim 17, wherein step b occurs in the presence of (benzotriazol-1-yloxy)-tris(pyrrolidino) phosphonium hexafluorophosphate.

19. A method according to claim 17, wherein the amino-substituted-tetrahydroisquinoline-benzotriazol is 7-amino-tetrahydroisquinoline-benzotriazol.

20. A method according to claim 17, wherein the amino-substituted-tetrahydroisoquinoline-ring compound comprises amino-substituted-tetrahydroisoquinoline-benzodiazepine, and step b comprises forming a support-bound intermediate having a nitro group and a protecting group by reacting the support-bound amino-substituted-tetrahydroisoquinoline-carboxylate with an amino-protected nitro-anthranilic acid, reducing the nitro group of the support-bound intermediate, reacting the support-bound intermediate with a reactant selected from the group consisting of acyl chlorides, solutions comprising a carboxylic acid and a N-protected amino acid, sulfonyl chlorides, isocyanates, isothiocyanates, epoxides, alkyl halides, aldehydes, and mixtures thereof, and removing the protecting group.

21. A method according to claim 20, wherein the amino-substituted-tetrahydroisoquinoline-benzodiazepine is 7-amino-tetrahydroisoquinoline-benzodiazpine.

22. A method of preparing a combinatorial library of amino-substituted-tetrahydroisoquinoline ring compounds; wherein said compound comprises a structure selected from the group consisting of:

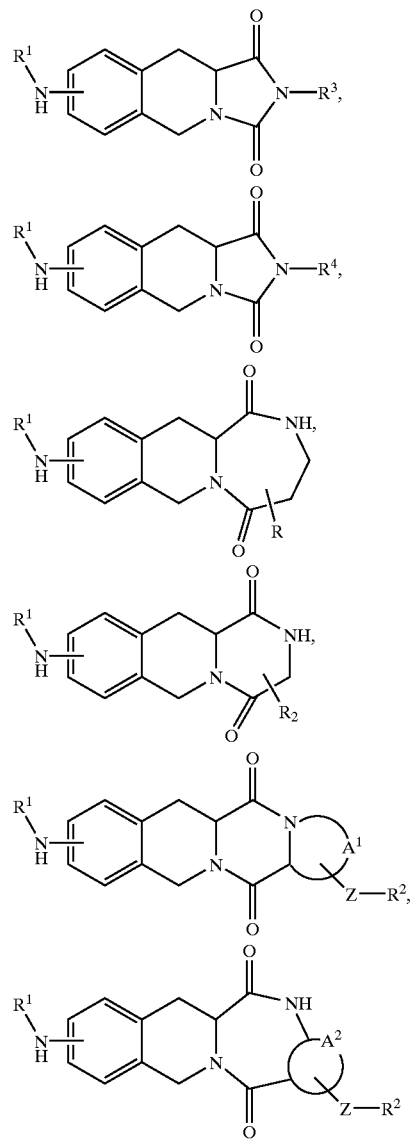

wherein

-continued

represents a heterocycle, aryl, or hydrocarbocycle;

represents a heterocycle; $R^1$ is alkyl, aryl, heterocyclic moiety, amide, sulfonamide, urea, thiourea, or alcohol and $R^2$ is alkyl, aryl, heterocyclic moiety, amide, sulfonamide, urea, thiourea, hydrogen, or alcohol; $R^3$ and $R^4$ are each independently an alkyl or aryl; n is from 0 to 1; $R^5$ is the side chain of an amino acid and Z is NH, O or S; wherein the amino acid side chain may be selected from the group consisting of side chains of natural and synthetic amino acids;

comprising the steps of (a) providing a support-bound amino-substituted-tetrahydroisoquinoline-carboxylic acid having the structure:

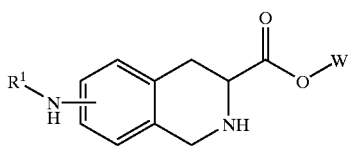

wherein W represents a solid support and $R^1$ is alkyl, aryl, heterocyclic moiety, amide, sulfonamide, urea, thiourea, or alcohol; (b) forming a first support-bound intermediate by reacting a first portion of a support-bound amino-substituted-tetrahydroisoquinoline carboxylic acid with a first reagent and forming a second support-bound intermediate by reacting a second portion of the support-bound amino-substituted-tetrahydroisoquinoline-carboxylic acid with a second reagent; and (c) cyclizatively cleaving the first and second support-bound intermediates to form first and second amino-substituted-tetrahydroisoquinoline ring compounds, respectively, wherein the first and second reagents are selected from the group consisting of (i) isocyanates having the structure $R^3NCO$ wherein $R^3$ is an alkyl or aryl, (ii) thioisocyanates having the structure $R^4NCS$ wherein $R^4$ is an alkyl or aryl, (iii) protected amino acids having the structure:

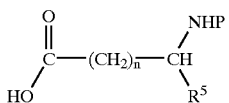

wherein P is a protecting group, n is from 0 to 1, and $R^5$ is the side chain of an amino acid, (iv) protected cyclic amino acids having the structure:

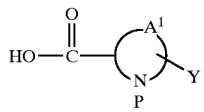

wherein represents a heterocycle, P is a protecting group, and Y is $NO_2$, NHP, OP, or SP and (v) protected cyclic amino acids having the structure:

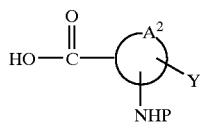

wherein

represents a heterocycle, aryl, or hydrocarbocycle, P is a protecting group, and Y is $NO_2$, NHP, OP, or SP; provided that when the first and second reagents are both isocyanates, the first reagent is a different isocyanate than the second reagent; when the first and second reagents are both thioisocyanates, the first reagent is a different thioisocyanate than the second reagent; when the first and second reagents are both protected non-cyclic amino acids, the first reagent is a different protected amino acid than the second reagent; and when the first and second reagents are both protected cyclic amino acids, the first reagent is a different protected cyclic amino acid than the second reagent.

* * * * *

UNITED STATES PATENT AND TRADEMARK OFFICE
CERTIFICATE OF CORRECTION

PATENT NO. : 6,608,193 B2
DATED : August 19, 2003
INVENTOR(S) : Song Liu et al.

It is certified that error appears in the above-identified patent and that said Letters Patent is hereby corrected as shown below:

Column 2,
Line 46, delete "R4NCS" and insert -- $R^4NCS$ --.

Column 21,
Line 9, delete

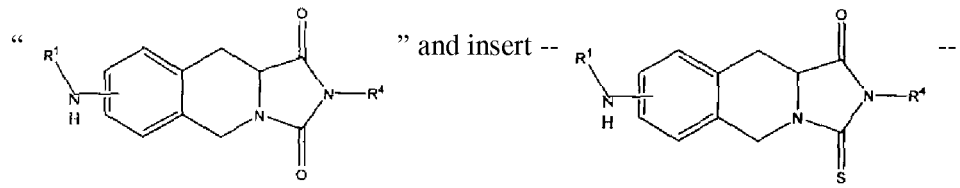

Signed and Sealed this

Twenty-second Day of February, 2005

JON W. DUDAS
*Director of the United States Patent and Trademark Office*